United States Patent
US 8,684,926 B2
Arndt
Apr. 1, 2014

(54) SYSTEM AND METHOD FOR KNOWLEDGE VERIFICATION UTILIZING BIOPOTENTIALS AND PHYSIOLOGIC METRICS

(75) Inventor: Craig M. Arndt, Alexandria, VA (US)

(73) Assignee: Ideal Innovations Incorporated, Arlington, VA (US)

(*) Notice: Subject to any disclaimer, the term of this patent is extended or adjusted under 35 U.S.C. 154(b) by 1191 days.

(21) Appl. No.: 12/389,722

(22) Filed: Feb. 20, 2009

(65) Prior Publication Data

US 2009/0216091 A1 Aug. 27, 2009

Related U.S. Application Data

(60) Provisional application No. 61/066,750, filed on Feb. 25, 2008.

(51) Int. Cl.
*A61B 5/00* (2006.01)
*G06F 19/00* (2011.01)

(52) U.S. Cl.
CPC .................................. *G06F 19/345* (2013.01)
USPC ............................ 600/301; 600/544; 434/236

(58) Field of Classification Search
USPC ............................ 600/300–301, 544; 434/236
See application file for complete search history.

(56) References Cited

U.S. PATENT DOCUMENTS

| | | | | |
|---|---|---|---|---|
| 5,406,956 A * | 4/1995 | Farwell | | 600/544 |
| 6,238,338 B1 * | 5/2001 | DeLuca et al. | | 600/300 |
| 7,565,193 B2 * | 7/2009 | Laken | | 600/544 |
| 8,014,847 B2 * | 9/2011 | Shastri et al. | | 600/410 |
| 2002/0062089 A1 * | 5/2002 | Johnson, Jr. | | 600/544 |
| 2004/0048232 A1 * | 3/2004 | Murphy et al. | | 434/322 |
| 2004/0143170 A1 * | 7/2004 | DuRousseau | | 600/300 |
| 2005/0089206 A1 * | 4/2005 | Rice et al. | | 382/128 |
| 2005/0143629 A1 * | 6/2005 | Farwell | | 600/300 |
| 2005/0283053 A1 * | 12/2005 | deCharms | | 600/300 |
| 2006/0149139 A1 * | 7/2006 | Bonmassar et al. | | 600/300 |
| 2006/0183981 A1 * | 8/2006 | Skinner | | 600/301 |
| 2007/0038035 A1 * | 2/2007 | Ehrlich et al. | | 600/300 |
| 2007/0049844 A1 * | 3/2007 | Rosenfeld | | 600/544 |
| 2007/0100216 A1 * | 5/2007 | Radcliffe et al. | | 600/300 |
| 2007/0191691 A1 * | 8/2007 | Polanco | | 600/301 |
| 2007/0249914 A1 * | 10/2007 | Cacioppo et al. | | 600/300 |

(Continued)

*Primary Examiner* — Bill Thomson
*Assistant Examiner* — Bobby Soriano
(74) *Attorney, Agent, or Firm* — Andrew Wichmann

(57) ABSTRACT

A system and method for knowledge verification utilizing biopotentials and physiologic metrics, which includes a computer-based device having stored thereon Probe, Relevant and Gallery image data, and a biopotential amplifier removably connected to a human subject via disposable Ag/Ag—Cl electrodes. Furthermore, the system comprises an analog-to-digital (A/D) converter to digitize said biopotential data for subsequent storage on said computer-based device, analysis software for discriminating said subject's event-related response to the exogenous stimuli, a visual display system comprising an LCD video monitor, and control software for presenting the Probe, Relevant and Gallery visual stimuli in a weighted, pseudo-random sequence which can be modulated by the outcome of said analysis software. Probe image data are not generally known to said human subjects but relevant to the knowledge to be verified; Relevant image data are generally known to said human subjects but not relevant to the knowledge to be verified; and Gallery image data are not generally known to said human subjects and not relevant to the knowledge to be verified. Said knowledge verification system can utilize parametric or non-parametric, e.g., artificial neural networks, analysis to provide an output of verification, or non-verification of knowledge of interest. Exemplary headband and electrode configurations optimized to produce the desired signals are disclosed.

14 Claims, 10 Drawing Sheets

(56) References Cited

U.S. PATENT DOCUMENTS

| | | | |
|---|---|---|---|
| 2007/0255122 A1* | 11/2007 | Vol et al. | 600/301 |
| 2008/0044799 A1* | 2/2008 | Krishna | 434/236 |
| 2008/0182231 A1* | 7/2008 | Cohen et al. | 434/350 |
| 2008/0214902 A1* | 9/2008 | Lee et al. | 600/301 |
| 2009/0024021 A1* | 1/2009 | George et al. | 600/411 |

* cited by examiner

SYSTEM AND METHOD FOR KNOWLEDGE VERIFICATION UTILIZING BIOPOTENTIALS AND PHYSIOLOGIC METRICS

CROSS-REFERENCE TO RELATED APPLICATIONS

This application claims the benefit of provisional patent application No. 61/066,750, filed 2008 Feb. 25 by the present inventor.

BACKGROUND

1. Field

The use of physiological methods to detect concealed information is as old as civilization. Even in ancient times observers noticed that whenever a crime suspect was being interrogated, the fear of possible exposure caused certain changes in his physiological functions. In ancient China a suspect was required to hold a quantity of rice in his mouth throughout the reading of his verdict. If the rice was still dry at the end, then the suspects guilt was considered proven since it was believed the fear of being exposed significantly reduced salivation in his mouth. Related techniques have been used throughout history by many very different peoples all over there world. However, modern "instrument-aided" physiological detection techniques did not arise until the early $20^{th}$ century.

2. Prior Art

William Marston, an American psychologist and attorney, stands apart from the rest of the early research community studying instrument-aided "lie detection." In 1913 the US National Research Committee formed a group of psychologists, including William Marston, to assess the potential use of known methods of lie detection for the needs of the counterintelligence service during World War I. Having conducted a substantial amount of research, the group concluded that the "blood pressure deception test" developed by Marston at Harvard University's psychology lab around 1913 was the most accurate method of all known at that time. Its accuracy in detecting lies was estimated to be as high as 97 percent. In 1923, John Marston, introduced for the first time, polygraph examination findings as proof of evidence in a court of law.

John Larson, a California police officer, designed the first practical prototype of a modern polygraph. After learning about Marston's "blood pressure deception test", Larson developed an instrument capable of continuously recording blood pressure, pulse and respiration. Larson then set about developing an interviewing protocol, which was called the Relevant/Irrelevant (R/I) procedure. Throughout the interrogation, he would sprinkle questions relevant to the crime ("Do you own a 0.38 revolver?") and questions that had nothing to do with it ("Are you twenty-eight years old?"). The assumption he made was that the innocent would have a similar physiological response to both types of questions, but guilty people would react more strongly to crime-relevant questions. The key problem with this approach was that even innocent people might be nervous, and crime-specific questions are generally fairly obvious. Nonetheless, a large number of criminal suspects were examined using this equipment, and highly accurate results were achieved.

Leonarde Keeler, working under Larson's guidance during the 1920s, played a crucial role in the deployment of the psycho-physiological method of lie detection in the United States. He came up with the first polygraph specifically designed to elicit hidden information (1933), the first guidebook on examination using a lie detector (1935), and founded a company for commercial production of these instruments. He also established the first training facility for polygraph examiners. Lastly, Mr. Keeler was the first to introduce polygraphy in the area of recruitment and crime prevention in business.

By the end of the 1930s three US companies were mass-producing lie detectors and marketing them throughout North America. Almost one hundred police departments in 28 states were making ample use of this instrument in their everyday work, and dozens of banks and commercial firms in the northern states introduced polygraphy for recruiting purposes and in-house investigations.

At about the time of the start of World War II the American Psychological Society undertook a special study to verify the reliability of polygraph examination in the interest of protecting the public. Having thoroughly analyzed the use of polygraph examinations in law-enforcement and the business environment, the research committee concluded that lie detection methods were sufficiently developed; the necessary technology existed; and a good number of well-trained specialists were available. Of these three factors, the last was considered most important. It was agreed that if a competent specialist was available, the examination results were quite useful. If such specialists were not available, it was concluded the method nor the equipment should be used.

At this point confidence in polygraphs started to increase and consequently their popularity did as well. Beginning in the early 1940s the polygraph was extensively used in protecting state secrets. Polygraphs were used in checking the personnel that had worked on the nuclear bomb project at the Oak Ridge Research Center.

Modern polygraphy consists of a computer system with bio-sensors. Sensors are used to measure and record a number of physiological changes that are related to the involuntary nervous system. The reliability of polygraphy is directly related to the number of measured and recorded inputs: typically the more inputs used, the more accurate the result. Decision-making is made by a trained expert human operator and is based on the aggregate of measurements taken, as well as individual characteristics.

Experts know that there is no direct connection between physical indicators and the sincerity of a person. Lie detectors record the level of involuntary nervous behavior of the examinee, but fail to identify the causative agent for changes measured by the instrument. The polygraph examiner has to make the final determination based on subjective input.

Functional Magnetic Resonance Imaging and Truth Detection

It has been known for over 100 years that changes in blood flow and blood oxygenation in the brain (collectively known as hemodynamics) are closely linked to neural activity. When nerve cells are active they consume oxygen carried by hemoglobin in red blood cells from local capillaries. The local response to this oxygen utilization is an increase in blood flow to regions of increased neural activity, occurring after a delay of approximately 1-5 seconds. This hemodynamic response rises to a peak over 4-5 seconds, before falling back to baseline (and typically undershooting slightly). This leads to local changes in the relative concentration of oxyhemoglobin and deoxyhemoglobin and changes in local cerebral blood volume in addition to change in local cerebral blood flow.

Hemoglobin is diamagnetic when oxygenated but paramagnetic when deoxygenated. The magnetic resonance (MR) signal of blood is therefore slightly different depending on the level of oxygenation. These differential signals can be detected using an appropriate MR pulse sequence, and manifest themselves as a blood-oxygen-level dependent (BOLD) contrast. Higher BOLD signal intensities arise from decreases in the concentration of deoxygenated hemoglobin since the blood magnetic susceptibility now more closely matches the tissue magnetic susceptibility. By collecting data in an MRI scanner with parameters sensitive to changes in magnetic susceptibility, one can assess changes in BOLD contrast. These changes can be either positive or negative depending upon the relative changes in both cerebral blood flow (CBF) and oxygen consumption. Increases in CBF that outstrip changes in oxygen consumption will lead to an increased BOLD signal. Conversely decreases in CBF that outstrip changes in oxygen consumption will cause a decreased BOLD intensity.

The precise relationship between neural signals and BOLD is still under active research. In general, changes in the BOLD signal are well correlated with changes in blood flow. Numerous studies during the past several decades have identified a coupling between blood flow and metabolic rate; that is, the blood supply is tightly regulated in space and time to provide the nutrients for brain metabolism. However, neuroscientists have been seeking a more direct relationship between the blood supply and the neural inputs/outputs that can be related to observable electrical activity and circuit models of brain function.

Although current data indicate that local field potentials, an index of integrated electrical activity, form a better correlation with blood flow than the spiking action potentials that are most directly associated with neural communication, no simple measure of electrical activity to date has provided an adequate correlation with metabolism and the blood supply across a wide dynamic range. Presumably, this reflects the complex nature of metabolic processes, which form a superset with regards to electrical activity. Some recent results have suggested that the increase in CBF following neural activity is not causally related to the metabolic demands of the brain region, but rather is driven by the presence of neurotransmitters, especially glutamate.

Some other recent results suggest that an initial small, negative dip before the main positive BOLD signal is more highly localized and also correlates with measured local decreases in tissue oxygen concentration (perhaps reflecting increased local metabolism during neuron activation). Use of this more localized negative BOLD signal has enabled imaging of human ocular dominance columns in primary visual cortex, with resolution of about 0.5 mm. One problem with this technique is that the early negative BOLD signal is small and can only be seen using larger scanners with magnetic fields of at least 3 Teslas. Further, the signal is much smaller than the normal BOLD signal, making extraction of the signal from noise that much more difficult. Also, this initial dip occurs within 1-2 seconds of stimulus initiation, which may not be captured when signals are recorded at long repetition (TR). If the TR is sufficiently low, increased speed of the cerebral blood flow response due to consumption of vasoactive drugs (such as caffeine) or natural differences in vascular responsivnesses may further obscure observation of the initial dip.

The BOLD signal is composed of CBF contributions from larger arteries and veins, smaller arterioles and venules, and capillaries. Experimental results indicate that the BOLD signal can be weighted to the smaller vessels, and hence closer to the active neurons, by using larger magnetic fields. For example, whereas about 70% of the BOLD signal arises from larger vessels in a 1.5 Tesla scanner, about 70% arises from smaller vessels in a 4 Tesla scanner. Furthermore, the size of the BOLD signal increases roughly as the square of the magnetic field strength. Hence there has been a push for larger field scanners to both improve localization and increase the signal. A few 7 Tesla commercial scanners have become operational, and experimental 8 and 9 Tesla scanners are under development.

BOLD effects are measured using rapid volumetric acquisition of images. Such images can be acquired with moderately good spatial and temporal resolution; images are usually taken every 1-4 seconds, and the sections in the resulting image typically represent cubes of tissue about 2-4 millimeters on each side in humans. Recent technical advancements, such as the use of high magnetic fields and advanced "multichannel" RF reception, have advanced spatial resolution to the millimeter scale. Although responses to stimuli presented as close together as one or two seconds can be distinguished from one another, using a method known as event-related functional Magnetic Resonance Imaging (fMRI), the full time course of a BOLD response to a briefly presented stimulus lasts about 15 seconds for the robust positive response.

The science behind fMRI lie detection has matured with astonishing speed. One of the pioneers in the field is Daniel Langleben, a psychiatrist at the University of Pennsylvania. Langleben developed a hypothesis that in order to formulate a lie, the brain first had to stop itself from telling the truth and then generate the deception—a process that could be mapped with fMRI. By analyzing time-sequenced BOLD signal sources, fMRI reveals the pathways that thoughts have taken through the brain. Langleben concluded in 2002 in a paper published in the journal NeuroImage that there is "a neurophysiological difference between deception and truth" that can be detected with fMRI.

The subject took on a new urgency after 9/11 as security shot to the top of the national agenda. Despite questions about reliability, the use of polygraph machines grew rapidly, both domestically—where the device is employed to evaluate government workers for security clearances—and in places like Iraq and Afghanistan, where polygraphers are deployed to extract confessions, check claims about weapons of mass destruction, confirm the loyalty of coalition officers, and grill spies. The Department of Defense Polygraph Institute (DoDPI) put out a call for funding requests to scientists investigating lie detection. Grants from DoDPI, the Department of Homeland Security, DARPA, and other agencies triggered a wave of research into new lie-detection technologies. Since the events of 9/11, there are now over 50 labs in the US alone doing this kind of research.

Langleben's team, whose work was funded partially by DARPA, began to focus on eliminating one major source of polygraph error—the subjectivity of the human examiner. Langleben and his colleagues developed pattern-recognition algorithms that identify deception in individual subjects by comparing their brain scans with those in a database of known liars. In 2005, both Langleben's lab and a DoDPI-funded team led by Andrew Kozel at the Medical University of South Carolina announced that their algorithms had been able to reliably identify lies.

Today's fMRI scanners are bulky, cost up to $3 million each, and in effect require consent because of their sensitivity to head movement. This technology is not considered applicable to individuals who might want to keep information concealed, and in spite of the advances made by Langleben in automating the detection of lies through sophisticated computer-based algorithms, the system still requires trained and skilled operators.

Evoked Potentials

In neurophysiology, an evoked potential is an electrical potential recorded from a human or animal (or "biopotential") following the presentation of a stimulus, as distinct from spontaneous potentials such as electroencephalograms or electromyograms. Evoked potential amplitudes tend to be low, ranging from less than a microvolt to several microvolts, compared to tens of microvolts for EEG, millivolts for EMG, and often close to a volt for EKG. To resolve these low-amplitude potentials against the background of ongoing EEG, EKG, EMG and other biological signals and ambient noise, signal averaging is usually required. The signal is time-synchronized to the stimulus and since most of the noise occurs randomly, the noise is averaged out.

Signals can be recorded from the cerebral cortex, brainstem, spinal cord and peripheral nerves. Usually the term "evoked potential" is reserved for responses involving either recording from, or stimulation of, central nervous system structures. Thus evoked CMAP (compound motor action potentials) or SNAP (sensory nerve action potentials) as used in NCV (nerve conduction studies) are generally not thought of as evoked potentials, though they do meet the above definition.

Sensory evoked potentials (SEP or SSEP) are recorded from the central nervous system following stimulation of sense organs (for example, visual evoked potentials elicited by a flashing light or changing pattern on a monitor; auditory evoked potentials by a click or tone stimulus presented through earphones) or by electrical stimulation of a sensory or mixed nerve. They have been widely used in clinical diagnostic medicine since the 1970s, and also in intraoperative neurophysiology monitoring (IONM), also known as surgical neurophysiology. There are three kinds of evoked potentials in widespread clinical use since the 1970s: auditory evoked potentials, usually recorded from the scalp but originating at brainstem level; visual evoked potentials, and somatosensory evoked potentials, which are elicited by electrical stimulation of peripheral nerves.

To measure evoked potentials electrodes need to be attached to various points of on the scalp. Typically, the head is measured using a standardized EEG measurement technique to determine the optimal locations (each location corresponding to a type of EP that will be measured—e.g. the two locations on the back of the skull for the visual cortex, etc.), which are typically marked with magic marker. Each of these spots is rubbed with an oil-removing scrub to get rid of the skin oil. Then an electrode dipped in a liberal quantity of conductive gel is applied to each location, and affixed with a strip of adhesive tape.

For visual evoked potentials (VEP), the subject is placed in front of a computer screen, which shows a pattern of white and black squares like a chessboard, and a red dot in the middle that the subject is supposed to focus his/her eyes on with minimal movement. The procedure is done one eye at a time, with the eye that is not being tested blocked off with an eye patch. During the actual procedure, these squares alternate (white ones become black, black ones become white) at a rate of several times a second. This produces responses in the visual cortex that are picked up by the electrodes. Since the computer controls the exact timing of the changes of the square colors, and receives the electrical response in the corresponding electrodes, it is able to determine precisely the amount of time it takes for the visual stimulus to reach the visual cortex. For the somatosensory evoked potentials (SEP), additional electrodes are applied, in the same manner as described earlier.

There are many things going on at once in the brain, so it is difficult to determine when the evoked potential from a particular stimulus arrives from just one stimulus. A common technique used to amplify the signal is called ensemble averaging. The stimulus in each evoked potential experiment is presented multiple times, and since other signal components besides the evoked potential are not related to the signal, the computer can discriminate and amplify the one consistent peak or series of peaks that are caused by the applied stimulus.

In the 1980's Towle, Heuer & Donchin demonstrated that a subject would produce a positive signal peak approximately 300 msec after onset of stimulus (P-300) in response to visual stimuli that consisted of two sets of photographs, one of generally known politicians, the other of generally known movie stars. The subjects were instructed to count one or the other category. Each time an image from the task-relevant class was displayed, the subject produced the traditional P-300 response. This research confirmed what was well known since the mid 1960's, primarily that P-300's are elicited by stimuli that provide information necessary for the performance of an explicit task assigned by the experimenter—such as counting movie stars. It was also accepted that P-300's would be not be present in the absence of such an explicit task.

In the late 1990's early 2000's Farwell et. al. hypothesized that stimuli that are not explicitly task-relevant would still nevertheless elicit a P-300 if they are particularly significant to the subject due to his/her past knowledge of the subject matter of the stimuli. This theory is based on the "Context Updating Model". This model is based on the idea that when a stimulus that is significant for the subject is provided, he or she can be expected to take particular note of it, thus revising his/her internal representation of the current environment and generating a P-300.

The Context Updating Model then provides an alternative means to ascertaining concealed knowledge of a human subject. In contrast to focusing on physiological changes elicited through an interrogative process, a new technique for verifying knowledge can be created by measuring the response to known-relevant stimuli which serve as a proxy for said knowledge. It is logical to assume that a human subject will produce one kind of signal in response to images of people, places and things for which he/she has knowledge and another kind of signal in response to images of people, places and things for which he/she has no knowledge.

There exist many methods using physiological metrics for the detection of concealed information. The prior art is replete with examples of various means and methods for ascertaining concealed knowledge of a human subject. Functional MRI has created a window to the mind permitting scientists to observe the areas of the brain and the neural pathways involved in lying. Many attempts, such as those disclosed by Farwell, utilize biopotentials including EEG in combination with an interrogative process to determine if information provided by a human user is truthful, or if it is part of a subterfuge. Almost every example of "Truth Detection" in the prior art have two important limitations that are overcome by the present invention: (1) The process involves an auditory or visual interrogation of the human subject, and (2) The system requires a skilled operator to administer the test and/or provide interpretation of the results. This is the case with modern polygraphy, functional MRI and other physiologically-based technologies.

Many inventors have devised myriad of approaches attempting to provide inexpensive, minimally invasive, and rapid knowledge verification systems which could detect concealed knowledge (typically guilty knowledge) of human users. However, none have succeeded in producing a system that is practical and desirable for use in applications where either no direct interrogation is desired, or no trained operator is available to administer the examination or provide expert analysis of the results. Because of these and other significant limitations, commercially viable automated knowledge verification systems have not yet come to market.

The present invention overcomes all of the aforesaid limitations by combining a system in which there is (1) no interrogation and (2) no subjective human-expert analysis with robust hardware elements such as a simple headband, a rugged biopotential amplifier, a fast microprocessor and a user-friendly automated software interface. The present invention utilizes an electrode-studded headband assembly that correctly positions an array of disposable Ag/Ag—Cl electrodes in the desired anatomical position along the Z-axis of the head of the subject. To apply, the operator places a dollop of conductive gel on the surface of each electrode, then lowers the band over and onto the subject's head and adjusts the tightness using Velcro straps. The leads from the headband are subsequently connected to the biopotential amplifier which is electrically attached to a computer such as a PC or laptop. In one potential embodiment, with the subject seated before the video monitor (which provides the stimulating visual images), the operator starts the control/analysis software, performs some simple calibration and test routines and begins the examination. During the examination, the software resident on the PC or laptop controls all aspects of the system's operation. At the end of the test, information relevant to the examination is provided to the operator in both electronic and hard-copy format.

This novel method of utilizing biopotentials coupled to the easy-to-use automated control/analysis software overcome many significant limitations of the prior art. Subjectivity and interpretation is not required with the present invention. Instead, the human-expert analysis of the prior art inventions is replaced by an objective software analysis algorithm. The only training required by the present invention is in its setup and operation—training that can be accomplished quickly and inexpensively.

It is an object of the present invention to overcome the problems, obstacles and deficiencies of the prior art.

It is also an object of the present invention to provide an improved system for verifying concealed knowledge of a human subject utilizing biopotentials and physiological metrics. It is further an object of the present invention to provide an improved system and method for enhancing the training of human subjects.

Accordingly, one embodiment of the present invention is directed to a system and method for verifying human knowledge by means of measuring subject's physiological responses to input stimuli comprising: (a) a stimuli exposure system that exposes the subject to input stimuli; (b) a sensor system that monitors and records subject's physiological responses before, during, and after input stimulus is presented to subject; (c) a computer system comprising processing and algorithmic elements that determines if subject's physiological responses indicate subject possesses knowledge of interest; and (d) a reporting system that presents a report to the operator which indicates: (i) input stimuli exposed to subject, (ii) physiological responses of the subject before, during, and after each input stimulus is exposed to subject, and (iii) determination of the computer system of whether subject possesses knowledge of interest.

The stimuli exposure system of this first embodiment includes Probe, Relevant and Gallery data; and a visual display comprising an LCD video monitor. A Protocol Creation Algorithm presents the probe, relevant and gallery visual stimuli in a weighted pseudo-random sequence. The Probe image data are not generally known to human subjects but relevant to the knowledge to be verified. The relevant image data are generally known to human subjects but not relevant to the knowledge to be verified. The gallery image data are not generally known to human subjects and not relevant to the knowledge to be verified.

Although exclusively visual stimuli are described in the first embodiment, alternative stimuli such as auditory, tactile, and olfactory stimuli may also be presented in other embodiments. These may be presented independently or in combination. The stimuli exposure system presents auditory stimuli through recorded audio playback. Tactile and olfactory stimuli are presented through physical samples.

The sensor system of this first embodiment includes a removable physiological data amplifier connected to a human subject via disposable Ag/Ag—Cl electrodes and an analog-to-digital (A/D) converter to digitize physiological data for subsequent storage on the computer system. Although this first embodiment reads specifically biopotential signals, additional physiological signals may also be monitored. These include functional magnetic resonance images or positron emission tomography. The data gathering would require the use of a Functional Magnetic Resonance Imaging (fMRI) machine or Positron Emission Tomography (PET) scanner.

The computer system of this first embodiment includes data analysis software. Analysis software discriminates subject's event-related response from exogenous stimuli by means of neural network analysis, parametric analysis, statistical analysis, pattern matching, or wavelet processing to provide an output of verification or non-verification of knowledge of interest. The reporting system presents the results of the determination of the data analysis software.

When an image is recognized, the user would be expected to produce a P-300 response indicative of said recognition. A predetermined number of instantiations of the Probe, Relevant and Gallery images would be ensemble averaged to ameliorate the contributions of artifacts. By examining the ratio of recognized-to-nonrecognized Probe and Gallery images, an objective metric for relevant knowledge verification could be realized. Statistical evaluation of the false-positives (incorrectly recognizing a Gallery image as a Probe image) and false-negatives (failing to correctly recognize a Probe image) for a specific subject would provide a determination with respect to subject's relevant knowledge. Relevant images provide benchmark measurements for recognized non-relevant images.

A second embodiment of the present invention is directed to a system and method for enhancing the training of human subjects in which subject's successful assimilation of information provided at a prior training event is verified by means of measuring subject's physiological responses to input stimuli. This second embodiment is comprised of the method and apparatus of the first embodiment in addition to a method wherein the results of the verification of subject's successful assimilation of information provided at a prior training event are used to determine if subject should repeat the training event. In addition, these results can be used to improve future training events.

With respect to this method, subject would complete a training exercise and subsequently be tested to verify relevant knowledge and determine retention. This test could be conducted using objective metrics. An electronic hand-operated switch could be optionally provided to the user to depress each time an image is recognized. Alternatively, subject could be asked to perform an abstract cognitive task such as a visualization task or counting task when an image is recognized. These results can further be utilized in modifying the training curriculum or training technique to optimize the exercise. If a particular set of information was not being taught well, the results of the test would show a consistent lack of knowledge in that area. The teaching methods for that area could then be changed in future training.

Other objects and advantages will be readily apparent to those of ordinary skill in the art upon viewing the drawings and reading the detailed description hereinafter.

DRAWINGS—FIGURES

DRAWINGS—REFERENCE NUMERALS

Figure 1:
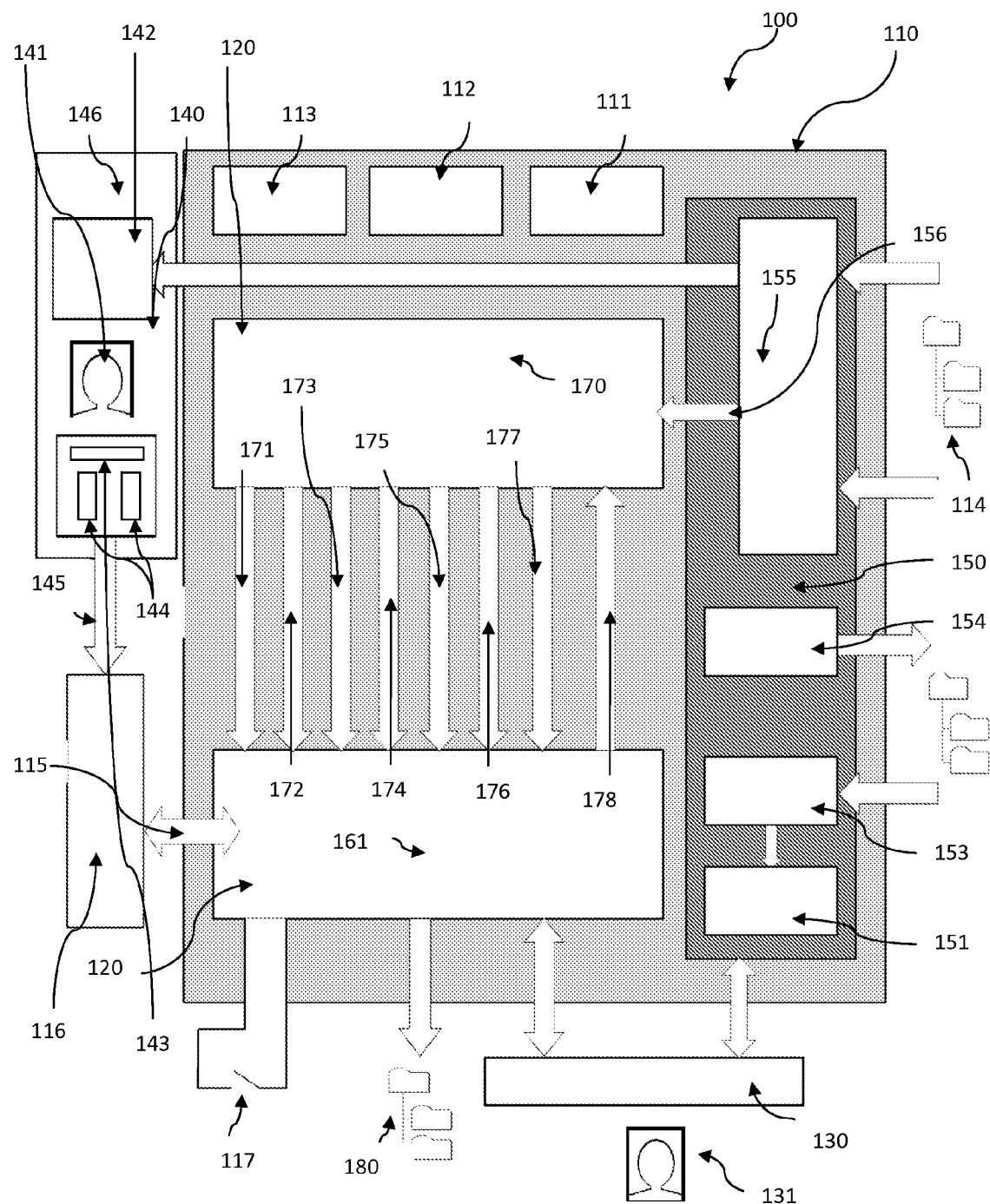
FIG. 1 shows a block diagram of the software architecture and hardware interfaces for the system design.

| DRAWINGS - Reference Numerals | |
|---|---|
| 100 computer-based device | 200 general processing steps |
| 300 headgear with biopotential sensors | 400 screening module |
| 500 knowledge tree | 600 gallery data |
| 700 event data tracing | 800 combined correlations plotting analysis |
| 900 neural network | 1000 flow chart |

DETAILED DESCRIPTION

Although those of ordinary skill in the art will readily recognize many alternative embodiments, especially in light of the illustrations provided herein, this detailed description is of the preferred embodiment of the present invention, a system and method for knowledge verification utilizing biopotentials and physiologic metrics.

In general, as shown in FIG. 1, a system and method for the verification of concealed knowledge of the present invention is referred to by the numeral 100 and generally comprises a computer-based device 110, software for performing the steps of the invention 120, operator control interface 130, and human subject interface 140.

Referring now specifically to FIG. 1, a system and method for knowledge verification utilizing biopotentials and physiologic metrics includes a computer 110 well known in the art and commercially available under such trademarks as IBM®, Compaq®, and Dell® having a central processor (CP) 111 that is well known in the art and commercially available under such trademarks as Intel® 486, Pentium®, and Motorola 68000, conventional non-volatile Random Access Memory (RAM) 112, conventional Read Only Memory (ROM) 113, and disk storage device(s) 114.

Computer 110 can be configured as a standard Personal Computer (PC) or can be implemented as a custom single-board computer utilizing an embedded operating system such as is sold commercially under the trademark Windows NT®. Computer 110 is operably associated with communications channel 115, which can be a conventional RS-232, USB or another equivalent bi-directional communications port. Communications channel 115 has associated therewith an Analog-to-Digital converter 116, which can be one of myriad devices that are known to anyone of ordinary skill in the art. The Analog-to-Digital converter 116 and communications channel 115 are responsible for converting the analog human biopotential signals into a digital representation that can be subsequently processed by computer 110. Computer 110 is further operably associated with disk storage device(s) 114 comprising a file system utilized in storing the images, protocols and human biopotential data 180. Computer 110 presents sequential images based on a testing protocol, described in detail herein below, to a human subject 141 via a video monitor 142 electrically associated with computer 110 which can be of an LCD type well known to anyone of ordinary skill in the art.

Human subject 141 has removably associated therewith Ag/Ag—Cl electrode array headgear 143, the particulars of which are described hereinafter. Two biopotential amplifiers 144 and an analog communications channel 145 that transmits three analog data types (Electroencephalogram (EEG), Electrooculogram (EOG), and Electromyogram (EMG)) is electrically associated with the Analog-to-Digital converter 116. Collectively, these elements (141 through 145) are housed in a subject isolation booth 146 designed to minimize artifacts caused by exogenous distractions and extraneous electrical noise. Graphical User Interface (GUI) 130 is also electrically associated with computer 110 and provides the control interface for the operator 131. GUI 130 would generally include a mouse, keyboard and monitor (not shown) for interacting with computer 110. Computer 110 is further electrically associated with an optional hand-operated switch 117 which can be located within the subject isolation booth 146 and used for certain protocols described hereinafter.

Computer 110 has programmably associated therewith software 120, which comprises a Wave Analysis Program 150, Wave Analysis Access Dynamic Link Library (DLL) 170, and Data Processing and Control Program 161, the particulars of which are further described hereinafter.

Wave Analysis Program 150 is comprised of Image Sequencing Logic algorithm 155, Protocol Creation Algorithm 154, Ensemble Averager 153, and parametric or non-parametric analysis algorithm(s) 151.

Image Sequencing Logic algorithm 155 is programmably associated with Liquid Crystal Display (LCD) video monitor 14, Wave Analysis Access DLL 170 and disk storage device(s) 114. Probe, Relevant, and Gallery images, described in detail herein below, are stored in the file system on disk storage device 114 and displayed to human subject 141 in a predetermined statistically weighted, pseudo-random sequence generated by Protocol Creation Algorithm 154. Image sequencing logic algorithm 155 is further programmably associated with Wave Analysis Access DLL 170 providing status updates via data conduit 156. This status data provides control and sequencing information to Data Processing and Control Program 161 via communications channels (171 through 178 inclusive) permitting time-synchronized data collection.

Wave Analysis Access DLL 170 is programmably associated with Data Processing and Control Program 161 through data conduits 171 through 178. These data conduits are comprised of Start Session 171, Start Recording 172, Image Displayed 173, Image Blanked 174, Stop Recording 175, Stop Session 176, Ready 177 and Start 178. In response thereto to signals sent via data conduits 171 through 178, Data Processing and Control Program 161 provides for the control and recordation of the human biopotential data 180 within disk storage device(s) 114.

Data Processing and Control Program 161 is electrically associated with communications port 115 and analog-to-digital converter 116, and is primarily responsible for controlling the data collection of human biopotential data 180 and processing and storing said data. Data Procession and Control Program 161 has programmably associated therewith a Lock-in Amplifier (LIS) algorithm, which is well known to anyone of ordinary skill in the art, and for the preferred embodiment, functions as a very-high Q filter. LIS algorithm computes a time-history of the power spectrum for a single predetermined frequency in near real-time. Multiple instantiations of LIS algorithm can be run concomitantly on PC 110, each with a unique pre-determined frequency. Since brain function produces signals that can be grouped into discrete bands of frequencies, LIS algorithm provides a way to discern information about what the brain is doing at any given point in time.

Including the raw EEG, EOG, and EMG data transmitted via communication channel 145 and data generated by LIS algorithm, Data Processing and Control Program 161 captures and records 26 simultaneous channels (13 for each bioamplifier 144) of data on disk storage device(s) 114. Finally, hand-operated switch 117 is electrically and programmably associated with Data Processing and Control Program 161 to provide an optional input from subject 141 that can be used for certain concealed knowledge verification protocols or for testing/calibration of system 100.

Figure 2:
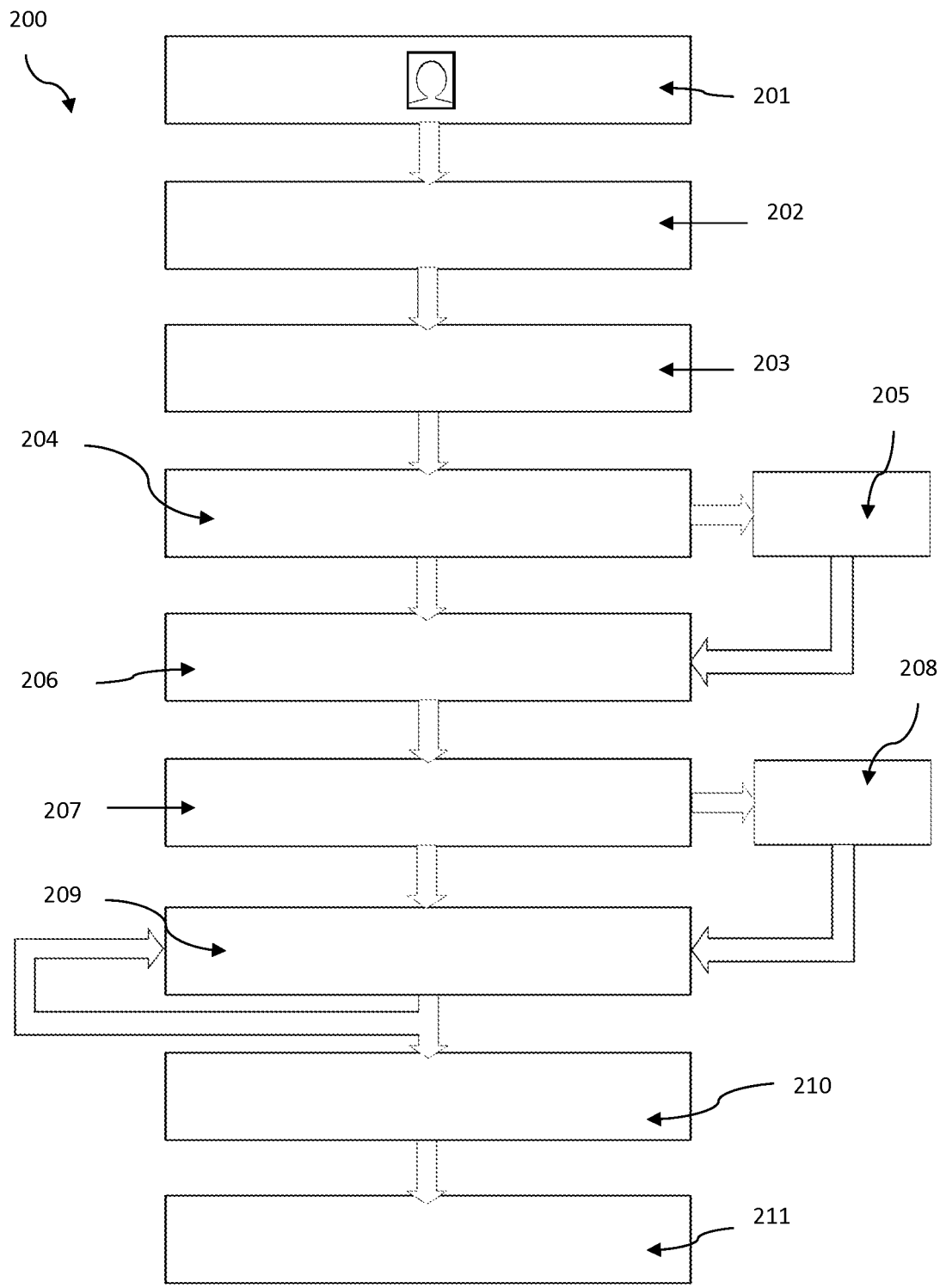
FIG. 2 shows in flow diagram a representation of the general processing steps of the concealed knowledge verification system.

As shown in FIG. 2, general processing steps 200 appropriate for implementation of the present invention include: preparing subject 201, calibrating bioamplifier 202, generating protocol for pass 1 203, and running initial screening module 204. At that point, the data is stored 205, the pass 2 protocols are generated 206, and subcategory paths are then run using decision trees 207. This data is stored for analysis 208, and the final analysis is completed 209. Based on this analysis, the subcategory paths are either rerun or human subject disconnects from headgear 210, and written report 211 is generated.

Figure 3:
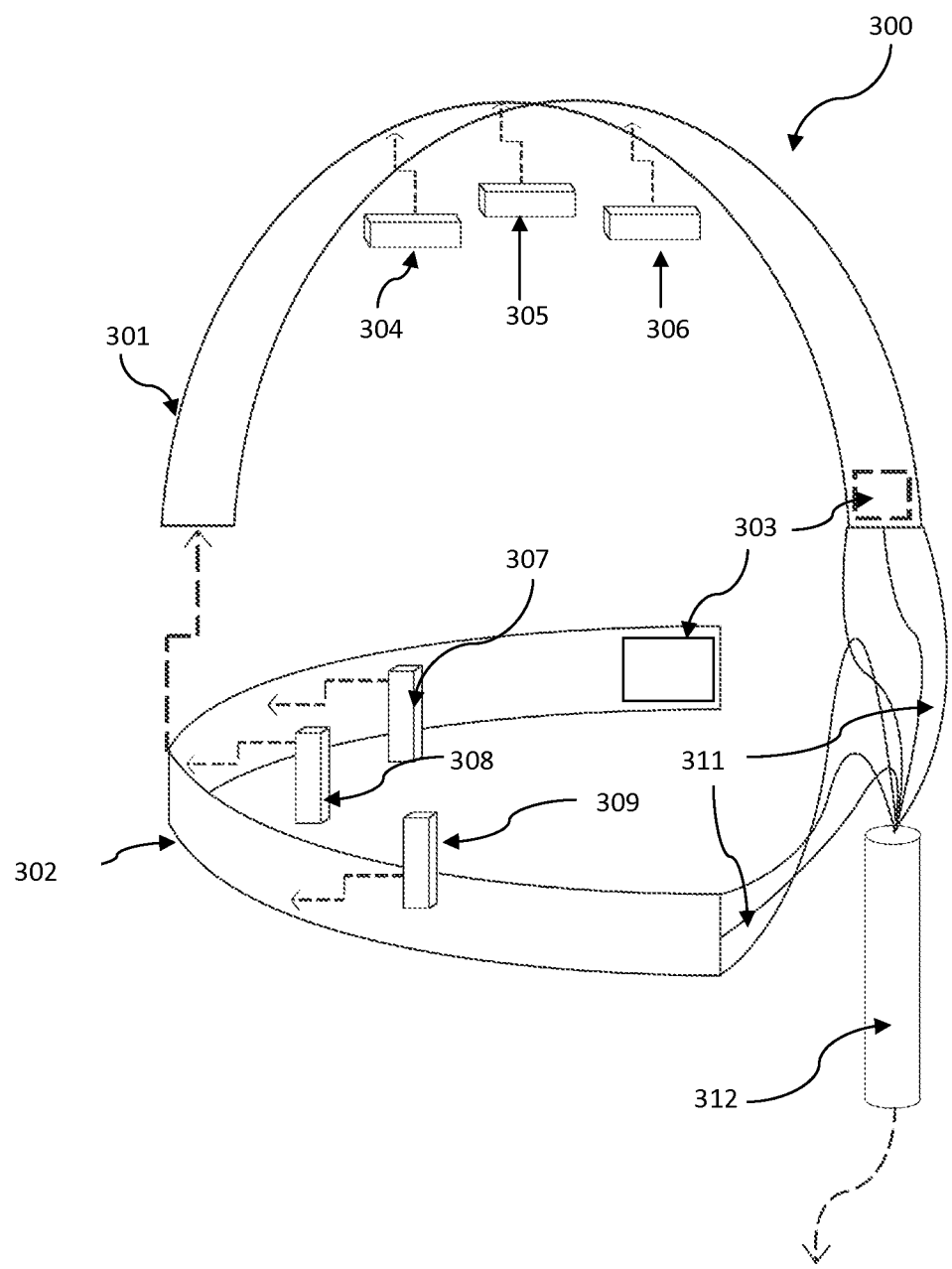
FIG. 3 shows in exploded view a representation of the headgear for the present invention.

FIG. 3 is a drawing of headgear 300 with biopotential sensors 304, 305, 306, 307, 308, and 309. Strap 301 mounts sensors to the top of the head, and strap 302 mounts them horizontally around the head from the front to the rear where it is attached at fastener 303. Transmission wires 311 transmit the biopotential signals to the biopotential amplifier 312.

Figure 4:
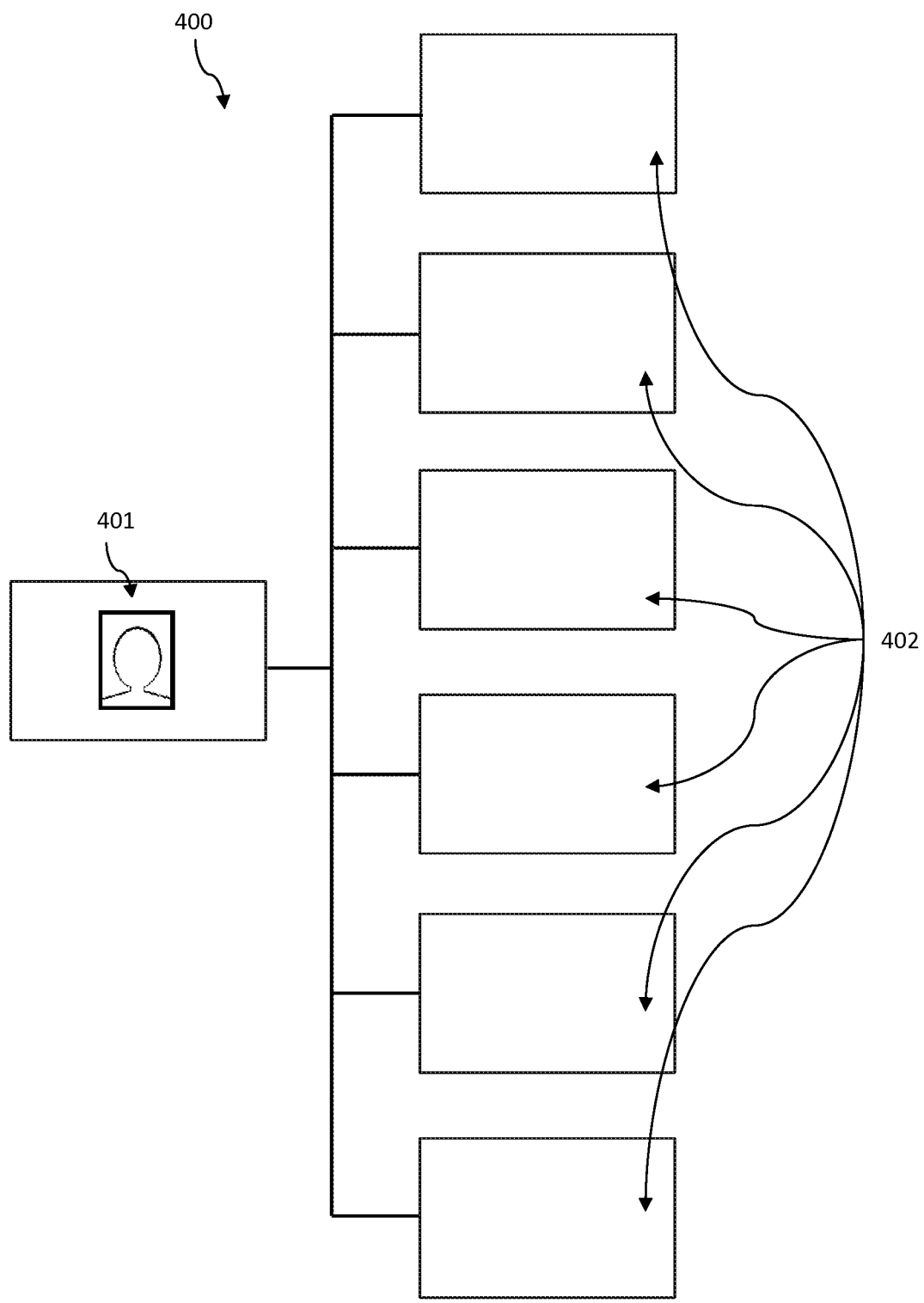
FIG. 4 shows in functional block diagram an exemplar screening module of the present invention.

FIG. 4 is a drawing of screening module 400 for this embodiment, indicating person of interest 401 and examples of categories of interest 402.

Figure 5:
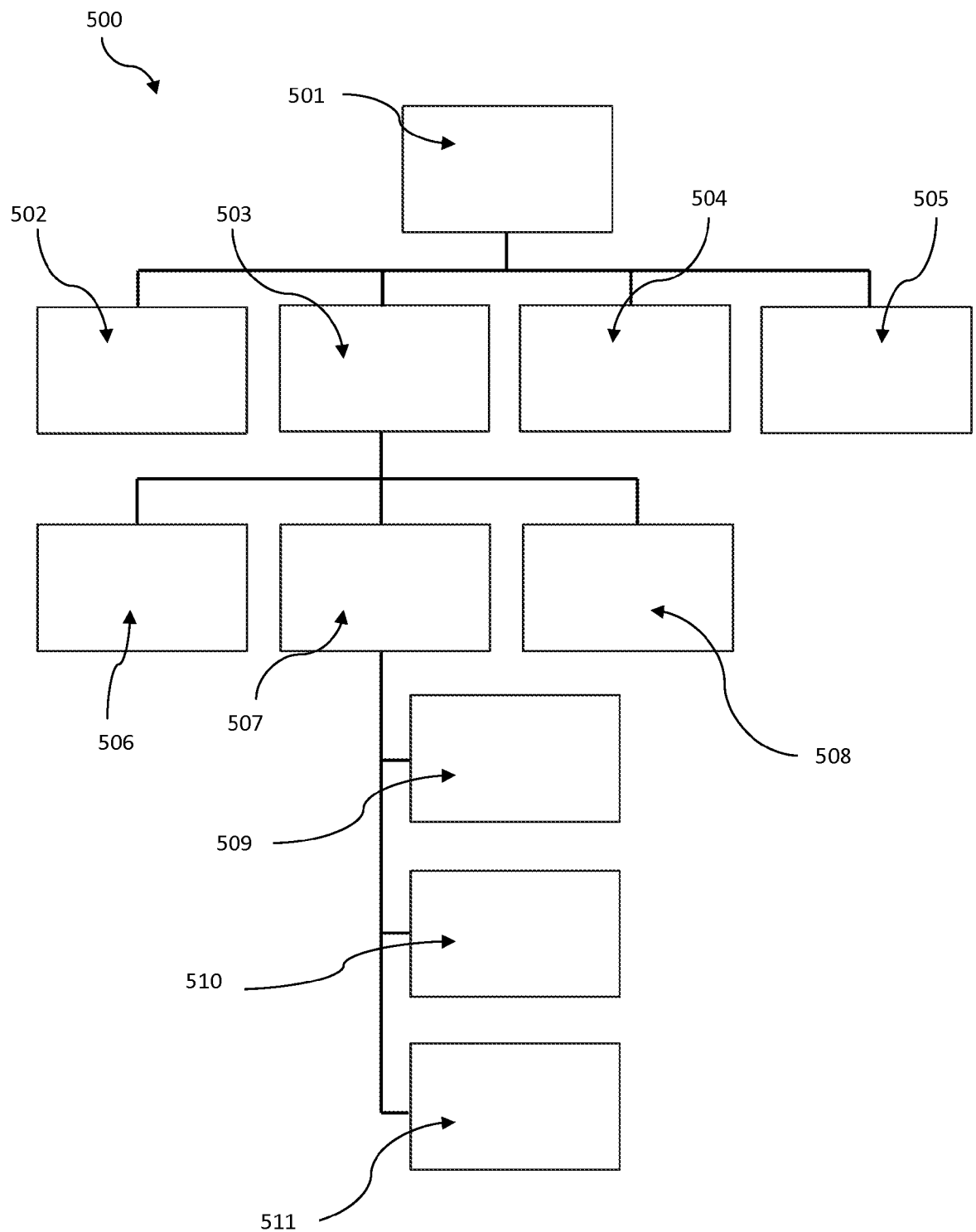
FIG. 5 shows in functional block diagram a dynamically adaptable knowledge tree utilized with the present invention.

FIG. 5 is an example of knowledge tree 500, which might be used in a subcategory routine. The highest level of the tree, weapons/contraband 501, represents the broadest level of indication, while specific ammunition 511, represents the most specific level of indication. If weapons/contraband 501 evokes a response, then artillery projectiles 502, handheld firearms 503, mortars-launchers 504, and mines/Explosively Formed Penetrators (EFPs) 505 will all be tested. If none of these stimuli evoke a response, then the tree will terminate with the weapons/contraband indication. However, if any of 502-505 evokes a response, then the routine will continue to work its way through Rocket Propelled Grenades (RPGs) 506, small arms 507, grenades 508, close-in pictures 509, disassembled parts 510, and specific ammunition 511 as long as at least one category on each level evokes a positive response.

Figure 6:
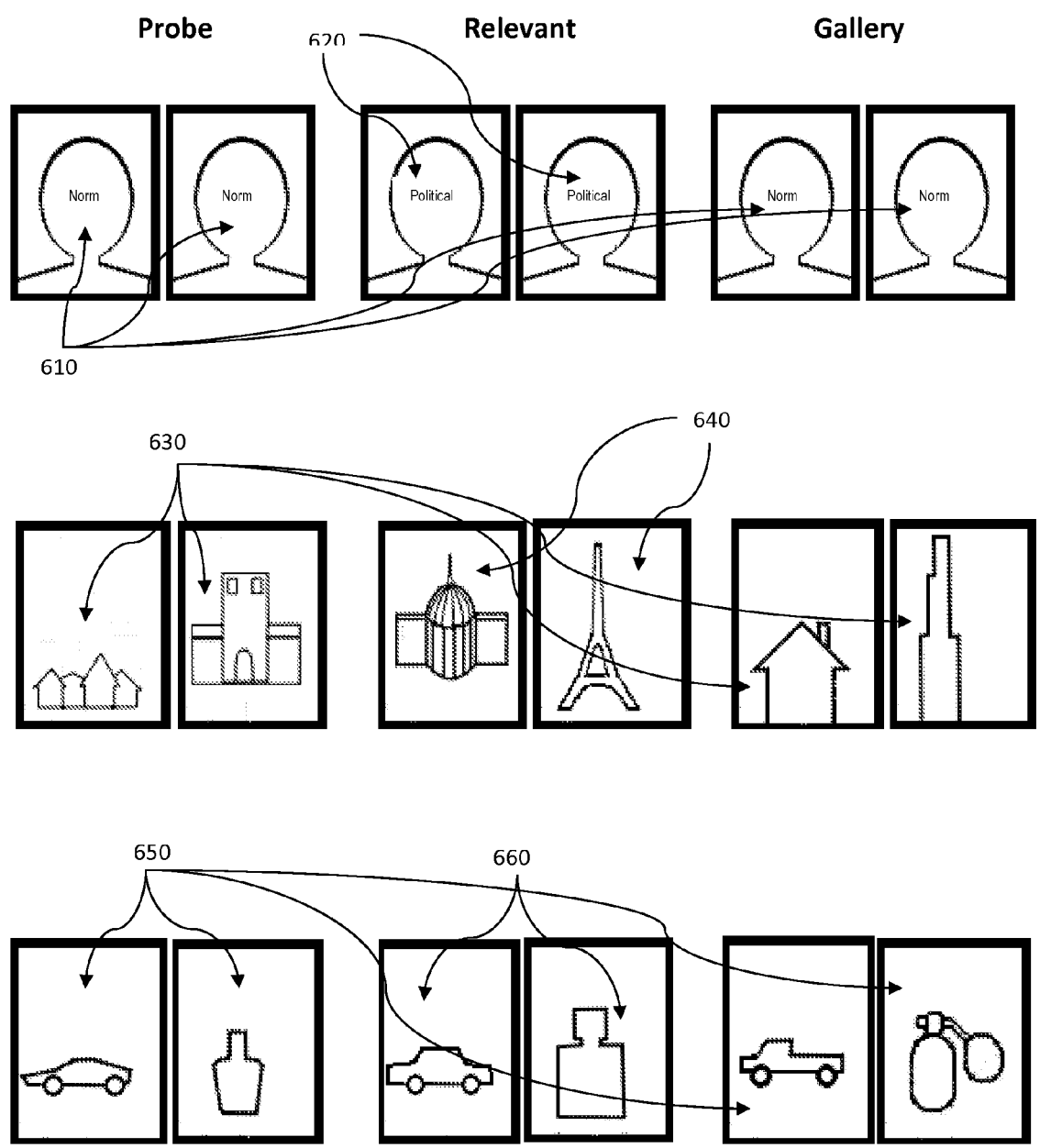
FIG. 6 shows in image form exemplars of the Probe, Relevant and Gallery images utilized with the present invention.

FIG. 6 is an example of possible sets of Probe, Relevant, and Gallery data. 610 represents normal individuals with whom human subject would generally not be familiar. 620 represents political figures of whom human subject would have knowledge. 630 represents common buildings about which human subject would generally not be familiar. 640 represents famous or iconic buildings about which human subject would have knowledge. 650 represents automobiles and perfume brands that human subject would not normally have encountered before. 660 represents famous or common automobiles and perfume brands that human subject would have knowledge of.

Figure 7:
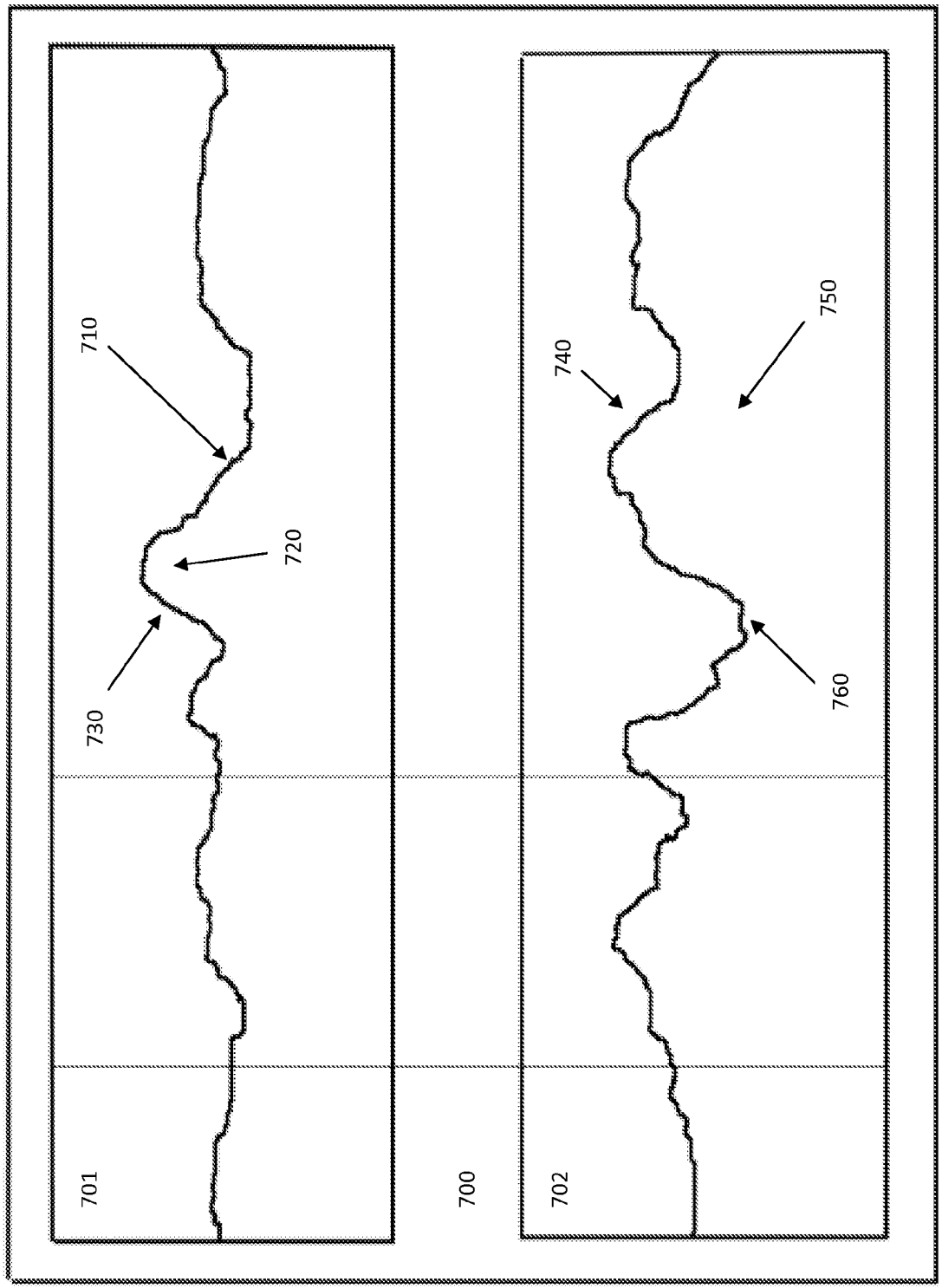
FIG. 7 shows an exemplar event data tracing of the present invention.

FIG. 7 is an example of event data tracing 700 from the present embodiment. 701 is the Sheep test. 710 indicates the return to normal pattern after the stimulus. 720 and 730 show the reaction to the stimulus without recognition of the content of the stimulus. 702 is the Wolf test. 760 shows the P300 recognition response to the stimulus, and 740 and 750 show the signal returning to a normal pattern.

Figure 8:
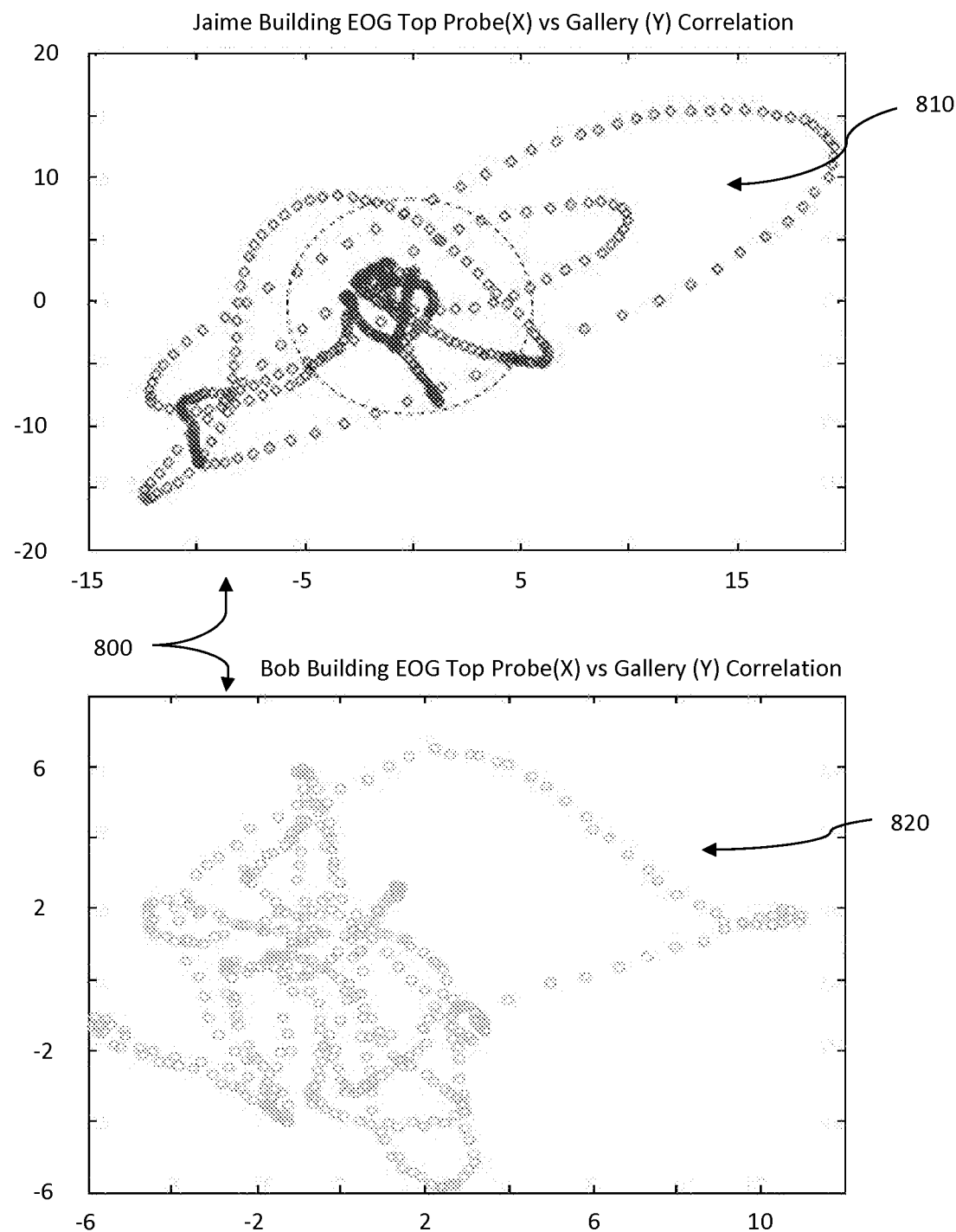
FIG. 8 shows in graphical form a representation of a parametric correlation plotting analysis technique of the present invention.

FIG. 8 includes diagrams of combined correlations plotting analysis 800 for the Sheep 810 and Wolf 820 tests of FIG. 7.

Figure 9:
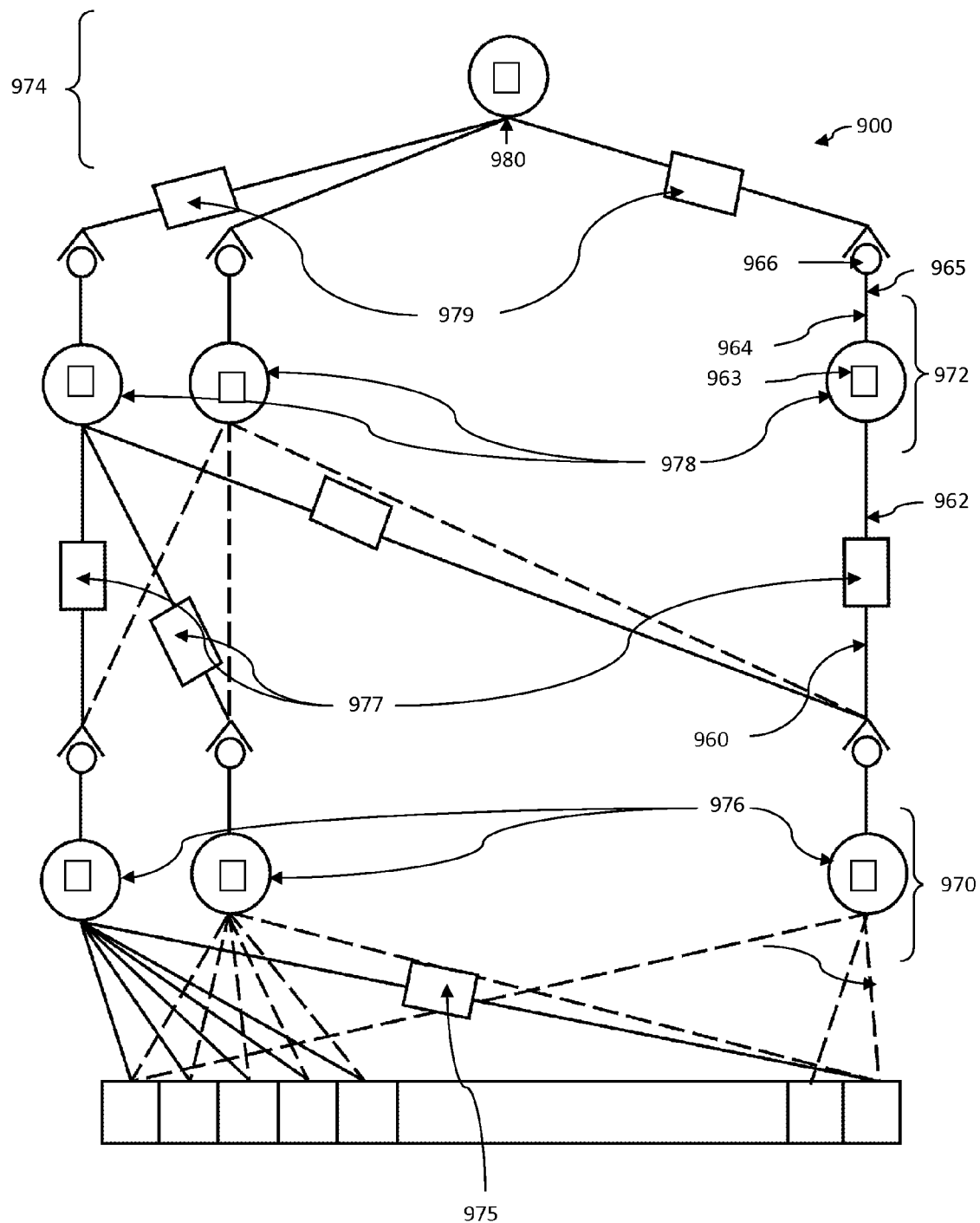
FIG. 9 shows in functional block diagram a representation of a neural network of the concealed knowledge verification system.

As shown in FIG. 9, the neural network 900 includes at least one layer of trained neuron-like units, and preferably at least three layers. The neural network 900 includes input layer 970, hidden layer 972, and output layer 974. Input layer 970, hidden layer 972, and output layer 974 include a plurality of trained neuron-like units 976, 978 and 980, respectively.

Neuron-like units 976 can be in the form of software or hardware. The neuron-like units 976 of the input layer 970 include a receiving channel for receiving human biopotential data, wherein the receiving channel includes modulator 975 for modulating the signal.

The neuron-like units 978 of the hidden layer 972 are individually receptively connected to each of the units 976 of the input layer 970. Each connection includes a predetermined modulator 977 for modulating each connection between the input layer 970 and the hidden layer 972.

The neuron-like units 980 of the output layer 974 are individually receptively connected to neuron-like units 978 of hidden layer 972. Each connection includes predetermined modulator 979 for modulating each connection between hidden layer 972 and output layer 974. Each unit 980 of said output layer 974 includes an outgoing channel for transmitting the output signal.

Each neuron-like unit 976, 978, and 980 includes dendrite-like unit 960, and preferably several, for receiving incoming signals. Each dendrite-like unit 960 includes modulator 975, 977, and 979, which modulates the amount of weight that is to be given to the particular characteristic sensed as described below. In dendrite-like unit 960, modulator 975, 977, and 979 modulate the incoming signal and subsequently transmit a modified signal 962. For software, dendrite-like unit 960 comprises an input variable X and a weight value W wherein the connection strength is modified by multiplying the variables together. For hardware, dendrite-like unit 960 can be a wire, optical or electrical transducer having a chemically, optically or electrically modified resistor therein.

Neuron-like units 976, 978, and 980 include soma-like unit 963, which has a threshold barrier defined therein for the particular characteristic sensed. When soma-like unit 963 receives modified signal 962, this signal must overcome the threshold barrier whereupon a resulting signal is formed. Soma-like unit 963 combines resulting signals 962 and equates the combination to output signal 964 indicative of the response to the collective inputs.

For software, soma-like unit 963 is represented by the sum $\Sigma = G_a X_a W_a - \beta$, where $\beta$ is the threshold barrier. This sum is employed in a Nonlinear Transfer Function (NTF) as defined below. For hardware, soma-like unit 963 includes a wire having a resistor; the wires terminating in a common point that feeds into an operational amplifier having a nonlinear component which can be a semiconductor, diode, or transistor.

Neuron-like unit 976, 978, and 980 include axon-like unit 965 through which the output signal travels, and also includes at least one bouton-like unit 966, and preferably several, which receive the output signal from axon-like unit 965. Bouton/dendrite linkages connect input layer 970 to hidden layer 972 and hidden layer 972 to output layer 974. For software, axon-like unit 965 is a variable which is set equal to the value obtained through the NTF and bouton-like unit 966 is a function which assigns such value to dendrite-like unit 960 of the adjacent layer. For hardware, axon-like unit 965 and bouton-like unit 966 can be a wire, an optical or electrical transmitter.

Modulators 975, 977, and 979, which interconnect each of the layers of neurons 970, 972, and 974 to their respective inputs, determine the classification paradigm to be employed by neural network 900. Human biopotential data are provided as inputs to the neural network and the neural network subsequently characterizes and generates an output signal in response thereto which is one of a categorization of the human biopotential data.

It is not exactly understood what weight is to be given to characteristics that are modified by the modulators of the neural network, as these modulators are derived through a training process defined below.

The training process is the initial process that the neural network must undergo in order to obtain and assign appropriate weight values for each modulator. Initially, modulators 975, 977, and 979 and the threshold barrier are all assigned small random, non-zero values. The modulators can each be assigned the same value, but the neural network's learning rate is best maximized if random values are chosen. Human biopotential data 180 are fed in parallel into the dendrite-like units of the input layer (one dendrite connecting to each data point of the human biopotential data 180) and the output observed.

The Nonlinear Transfer Function (NTF) employs a gain factor g in the following equation to arrive at the output:

$$NTF = 1/[1+e^{-g}]$$

For example, in order to determine the amount weight to be given to each modulator for any given human facial image, the NTF is employed as follows:

If the NTF approaches 1, the soma-like unit produces an output signal indicating a strong response. If the NTF approaches 0, the soma-like unit produces an output signal indicating a weak response. If the output signal clearly conflicts with the known empirical output signal, an error occurs. The weight values of each modulator are adjusted using the following formulas so that the input data produces the desired empirical output signal.

For the output layer:

$$W^*_{kol} = W_{kol} + GE_k Z_{kos}$$

$W^*_{kol}$=new weight value for neuron-like unit k of the outer layer
$W^*_{kol}$=current weight value for neuron-like unit k of the outer layer
G=gain factor
$Z_{kos}$=actual output signal of neuron-like unit k of output layer
$D_{kos}$=desired output signal of neuron-like unit k of output layer
$E_k = Z_{kos}(1-Z_{kos})(D_{kos}-Z_{kos})$, (this is an error term corresponding to neuron-like unit k of outer layer).

For the hidden layer:

$$W^*_{jhl} = W_{jhl} + GE_j Y_{jos}$$

$W^*_{jhl}$=new weight value for neuron-like unit j of the hidden layer.
$W_{jhl}$=current weight value for neuron-like unit j of the hidden layer.
G=gain factor
$Y_{jos}$=actual output signal of neuron-like unit j of hidden layer.
$E_j = Y_{jos}(1-Y_{jos})E_k(E_k * W_{kol})$, (this is an error term corresponding to neuron-like unit j of hidden layer over all k units).

For the input layer:

$$W^*_{iil} = W_{iil} + GE_i X_{ios}$$

$W^*_{iil}$=new weight value for neuron-like unit I of input layer.
$W_{iil}$=current weight value for neuron-like unit I of input layer.
G=gain factor
$X_{ios}$=actual output signal of neuron-like unit I of input layer.
$E_i = X_{ios}(1-X_{ios})E_j(E_j * W_{jhl})$, (this is an error term corresponding to neuron-like unit of input layer over all j units).

The training process consists of entering new (or the same) exemplar data into neural network 900 and observing the output signal with respect to a known empirical output signal. If the output is in error with what the known empirical output signal should be, the weights are adjusted in the manner described above. This iterative process is repeated until the output signals are substantially in accordance with the desired (empirical) output signal, and then the weight of the modulators are fixed. Upon fixing the weights of the modulators, the neural network is then trained and can make generalizations about human biopotential input data that is new to the neural network.

The description provided for neural network 900 as utilized in the present invention is but one technique by which a neural network algorithm can be employed. It will be readily apparent to those who are of ordinary skill in the art that numerous neural network paradigms including multiple (sub-optimized) networks, as well as numerous training techniques, can be employed to obtain equivalent results to the method as described herein above. In addition, myriad techniques for preprocessing said human biopotential input data can be employed to better prime the data for presentation to a neural network algorithm. These techniques can help create an input signal that is scale-normalized and translationally invariant and subsequently reduce error contributions due to the sensitivity of neural networks to these parameters.

Figure 10:
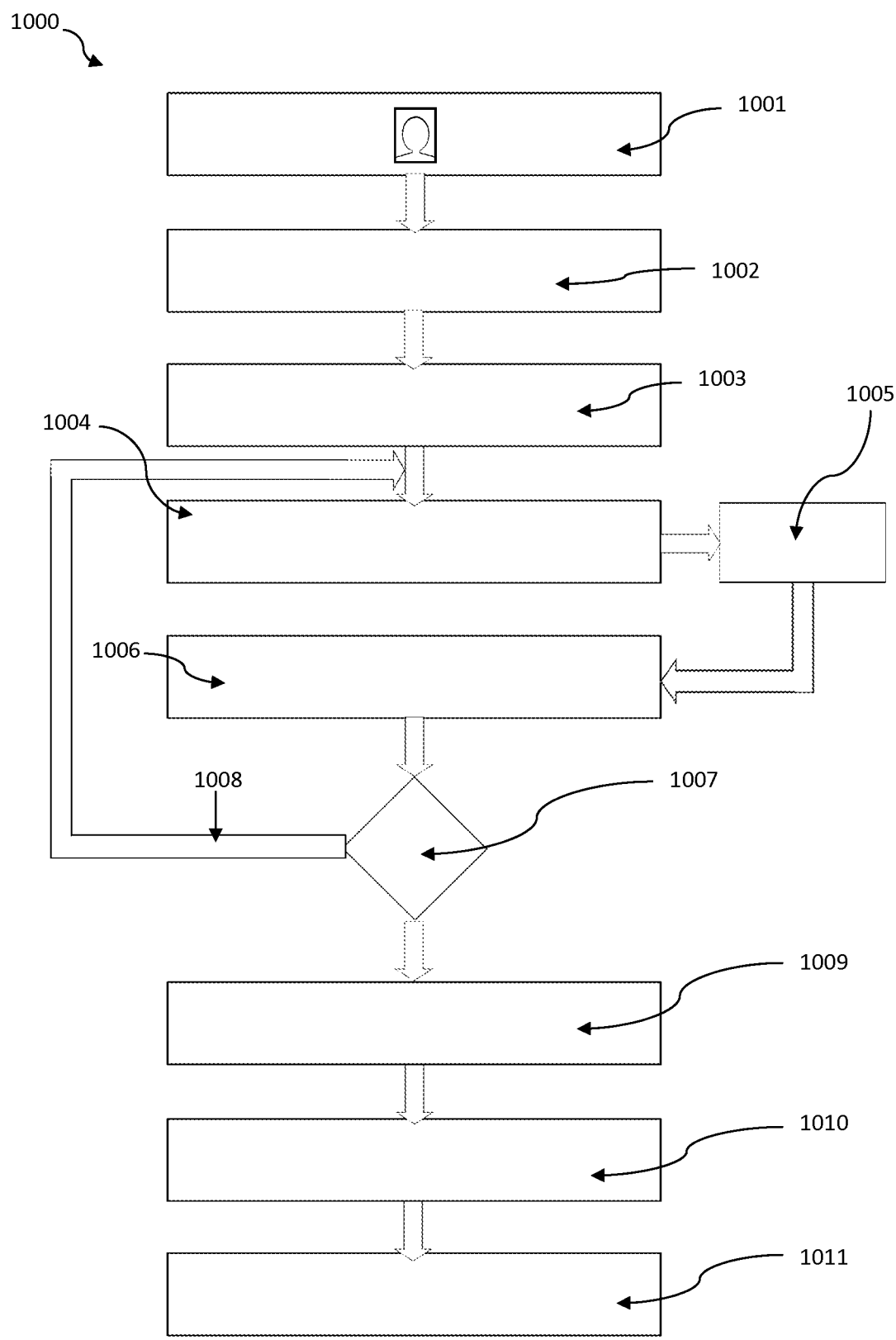
FIG. 10 shows in flow diagram a representation of the general processing steps of another aspect of the present invention for monitoring and enhancing training.

FIG. 10 contains flow chart 1000 for a system and method for monitoring and enhancing student training programs. First the subject is prepared 1001, the bioamplifier is calibrated 1002, and a protocol for evaluating the first area of training knowledge is generated 1003. Then knowledge verification run module 1004 executes and the results of the data are stored 1005. At step 1006, the additional knowledge verification run modules may execute if there are additional knowledge areas to test. After there are no further knowledge areas to test, the results of the test are evaluated on a pass/fail basis at 1007. If the subject did not pass, then he or she will have to repeat the sequence of run modules at a later time at 1008. If the subject did pass, then the final analysis is completed at 1009 and he or she is disconnected at 1010. Lastly, a written report is generated based on the results of final analysis 1011.

The above described embodiments are set forth by way of example and are not for the purpose of limiting the scope of the present invention. It will be readily apparent to those or ordinary skill in the art that obvious modifications, derivations and variations can be made to the embodiments without departing from the scope of the invention. For example, the automated human biopotential analysis software described herein above as either non-parametric analysis algorithm, such as neural network, or parametric analysis algorithm could also be one of a statistical based system, template or pattern matching, or even rudimentary wavelet processing techniques whereby the characteristics of the biopotential signals are analyzed. Similarly, the data processing and control program described in detail above as utilizing lock-in amplifier, could be one of many other algorithms well known to anyone of ordinary skill in the art.

The invention claimed is:

1. A knowledge verification method, comprising
presenting probe, relevant, and gallery data to a subject in a statistically weighted, pseudo-random sequence through a data processing and control program operating on a computer;
recording, in storage on the computer, a time history of the presentation of the probe, relevant, and gallery data;
recording, in storage on the computer, while the subject is experiencing the presentation of the probe, relevant, and gallery data, electrical activity in the subject's brain that is measured by one or more electrodes operatively connected to the computer;
analyzing the electrical activity through a neural network operating on the computer to determine if the electrical activity contains one or more p-300 responses; and
determining whether any p-300 responses are correlated with the subject experiencing the probe data by comparing, through the data processing and control program operating on the computer, the occurrence of any p-300 responses to the time history of the probe, relevant, and gallery data presented to the subject.

2. The method of claim 1, wherein the presenting probe, relevant, and gallery data to the subject takes place while the subject is in an isolation booth that substantially reduces exogenous distractions and extraneous electrical noise.

3. The method of claim 1, wherein the presenting probe, relevant, and gallery data proceeds according to a knowledge tree where the broadest category of probe data is presented first and more specific categories of the same general category of probe data are only presented if broader categories evoke a p-300 response.

4. The method of claim 1, wherein the electrical activity measured by the one or more electrodes is converted into a digital representation by an analog-to-digital converter.

5. The method of claim 1, wherein the neural network employs at least three layers of neuron-like units.

6. The method of claim 1, wherein the neural network employs ensemble averaging.

7. The method of claim 1, wherein the neural network employs one or more weighted modulators between each layer of neuron-like units.

8. A knowledge verification system, comprising
one or more electrodes;
a computer having storage and a monitor, and configured to perform the steps of
presenting probe, relevant, and gallery data to a subject in a statistically weighted, pseudo-random sequence through a data processing and control program operating on the computer;
recording, in storage on the computer, a time history of the presentation of the probe, relevant, and gallery data;
recording, in storage on the computer, while the subject is experiencing the presentation of the probe, relevant, and gallery data, electrical activity in the subject's brain that is measured by the one or more electrodes operatively connected to the computer;
analyzing the electrical activity through a neural network operating on the computer to determine if the electrical activity contains one or more p-300 responses; and
determining whether any p-300 responses are correlated with the subject experiencing the probe data by comparing, through the data processing and control program operating on the computer, the occurrence of any p-300 responses to the time history of the probe, relevant, and gallery data presented to the subject.

9. The system of claim 8, comprising an isolation booth that substantially reduces exogenous distractions and extraneous electrical noise.

10. The system of claim 8, wherein the presenting probe, relevant, and gallery data proceeds according to a knowledge tree where the broadest category of probe data is presented first and more specific categories of the same general category of probe data are only presented if broader categories evoke a p-300 response.

11. The system of claim 8, wherein the electrical activity measured by the one or more electrodes is converted into a digital representation by an analog-to-digital converter.

12. The system of claim 8, wherein the neural network employs at least three layers of neuron-like units.

13. The system of claim 8, wherein the neural network employs ensemble averaging.

14. The system of claim 8, wherein the neural network employs one or more weighted modulators between each layer of neuron-like units.

* * * * *